(12) United States Patent
Dau et al.

(10) Patent No.: US 10,733,270 B2
(45) Date of Patent: Aug. 4, 2020

(54) TECHNIQUES FOR GENERATING TRAINING SUGGESTIONS

(71) Applicant: Under Armour, Inc., Baltimore, MD (US)

(72) Inventors: Nathan Dau, Keswick, VA (US);
Jeffrey Allen, Baltimore, MD (US);
Mark A. Oleson, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 153 days.

(21) Appl. No.: 15/607,817

(22) Filed: May 30, 2017

(65) Prior Publication Data

US 2018/0349562 A1   Dec. 6, 2018

(51) Int. Cl.
| | | |
|---|---|---|
| G08B 23/00 | (2006.01) | |
| G06F 19/00 | (2018.01) | |
| G06F 1/16 | (2006.01) | |
| H04B 1/3888 | (2015.01) | |
| H04W 4/80 | (2018.01) | |
| H04B 1/3827 | (2015.01) | |
| H04W 4/00 | (2018.01) | |

(52) U.S. Cl.
CPC .......... G06F 19/3481 (2013.01); G06F 1/163 (2013.01); H04B 1/385 (2013.01); H04B 1/3888 (2013.01); H04W 4/00 (2013.01); H04W 4/80 (2018.02)

(58) Field of Classification Search
CPC .... G06F 19/3481; G06F 1/1626; G06F 1/163; H04W 4/00; H04W 4/80; H04B 1/385; H04B 1/3888; G09B 5/06; G09B 19/0092; G09B 19/00; G09B 5/02; G06Q 10/10; G06Q 10/0639; G06Q 50/01; G16H 20/40; G16H 40/63; G06T 13/40; G06T 19/00; G06T 2219/2012; A61B 5/11; A61B 5/165; A61B 5/02055; A61B 5/744; A61B 5/7264; A61B 5/0205; A61B 5/7445; A61B 5/45; A61B 5/43; A61B 5/41; A61B 5/486; A61B 5/42; A61B 5/40; A61B 5/20; A61B 5/7246; A61B 5/44; A61B 5/08
USPC ............. 340/521, 573.1, 574, 573.7, 539.11, 340/539.12; 600/508
See application file for complete search history.

(56) References Cited

U.S. PATENT DOCUMENTS

| | | | |
|---|---|---|---|
| 2016/0086500 A1* | 3/2016 | Kaleal, III | .............. G06T 19/00 434/257 |
| 2016/0242654 A1* | 8/2016 | Quinlan | ................ A61B 5/1123 |
| 2017/0011223 A1* | 1/2017 | Dang | .................... G06F 21/606 |
| 2017/0281082 A1* | 10/2017 | Khine | ................ A61B 5/02055 |

* cited by examiner

*Primary Examiner* — Anh V La

(57) ABSTRACT

An aspect of the present invention is drawn to a patch for use with application against the skin of a user. The patch includes a substrate, a material detector, a memory, a comparator, an output component, and a power source. The material detector is disposed on the substrate and has a contact portion disposed so as to contact the skin. The material detector generates a material signal based on the amount of material contacting the contact portion. The memory has a priori material data stored within. The comparator outputs a compared signal based on the comparison of the material signal and the a priori material data. The output component outputs a readiness signal based on the compared signal and the a priori data. The power source provides power to the output component.

17 Claims, 4 Drawing Sheets

TECHNIQUES FOR GENERATING TRAINING SUGGESTIONS

BACKGROUND

The present invention generally relates to using a patch to generate a training suggestion based on the readiness evaluation of a user's physical state.

There exists a need for a device and method for generating a training suggesting based on the readiness of a user.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Overview

An aspect of the present invention is drawn to a patch for use with application against the skin of a user. The patch includes a substrate, a material detector, a memory, a comparator, an output component, and a power source. The material detector is disposed on the substrate and has a contact portion disposed so as to contact the skin. The material detector generates a material signal based on the amount of material contacting the contact portion. The memory has a priori material data stored within. The comparator outputs a compared signal based on the comparison of the material signal and the a priori material data. The output component outputs a readiness signal based on the compared signal and the a priori data. The power source provides power to the output component.

EXAMPLE EMBODIMENTS

Fitness planners are a popular method of creating training regimens with a large variety of goals such as losing weight, building muscle, increasing strength, or endurance training. In general, a training regimen that is created by a fitness planner will instruct a user to perform an activity for a given amount of time based on his current physical state and goals.

For example, suppose a person who is in average physical shape would like to use a fitness planner to create a training regimen so that they may run a five kilometer race three months away. The training regimen would then instruct the user to perform an activity such as strength training, a three, five or seven kilometer run, or sprints for each training day leading up to the five kilometer race. Since the daily activity in the training regimen is set in advance, there is no way to take into account the physical state of the user while training, which may lead to the user overexertion and physical harm.

Figure 1:
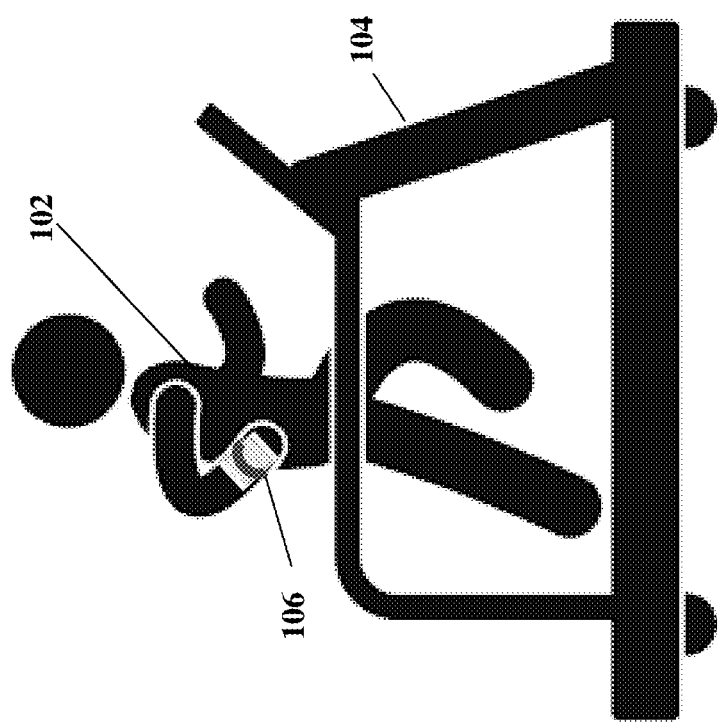
FIG. 1 illustrates a block diagram of a user running.

FIG. 1 illustrates a block diagram 100 of a user running as dictated by a training regimen created using a conventional fitness planner.

As illustrated in the figure, block diagram 100 includes a user 102, a treadmill 104, and a phone 106.

User 102 runs on treadmill 104. User 102 uses phone 106 to track the distance they have run while running on treadmill 104.

In operation, user 102 is following a training regimen that was created in advance using a conventional fitness planner that does not consider the physical state of the user. In this example embodiment, the training regimen that was created instructs user 102 to run for five miles. At this time, user 102 begins running on treadmill 104 and uses phone 106 to track the distance they have run.

In this example embodiment, suppose that user 102 has not been drinking enough electrolytes and their sodium levels are very low before they begin running. It is possible that as user 102 runs, they will lose even more sodium and their physical state will decline rapidly, resulting in user 102 only being able to run two miles instead of five.

In this case, the training regimen will not compensate for user 102 failing to run the entire five miles, which will lead user 102 to fall behind their regimen. Further, each time user 102 fails to complete the predetermined amount of activity; their deficiency is compounded until they are unable to keep up with their training regimen at all.

Figure 2:
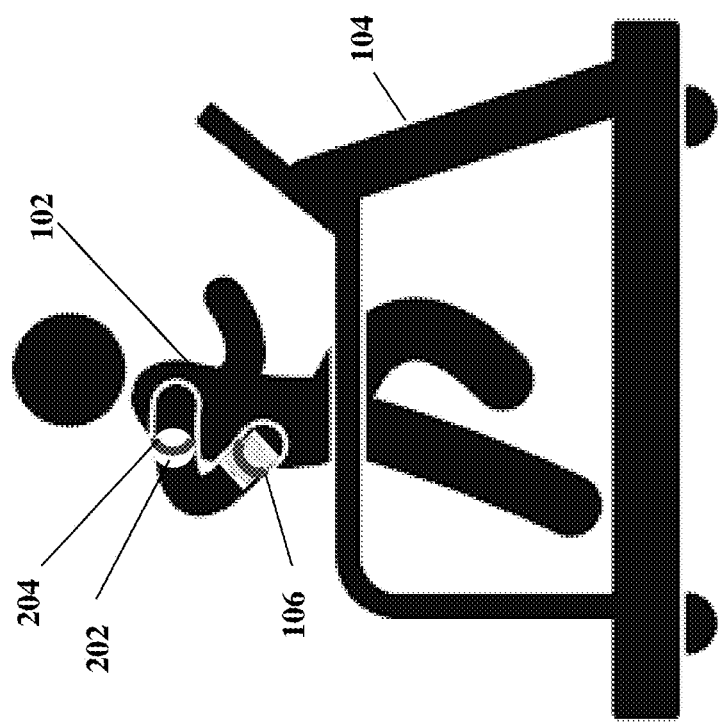
FIG. 2 illustrates a block diagram of a user using a patch in accordance with aspects of the present invention.

FIG. 2 illustrates a block diagram 200 of a user using a patch in accordance with aspects of the present invention.

As illustrated in the figure, block diagram 200 includes user 102, treadmill 104, phone 106, a patch 202, and an article of clothing 204.

User 102 runs on treadmill 104. User 102 uses phone 106 to track the distance they have run while running on treadmill 104.

Patch 202 indicates the physical state of user 102.

Article of clothing 204 is operable to apply pressure in order to keep patch 202 pressed against the skin of user 102. Article of clothing 204 may be one of the group consisting of an arm sleeve, a leg sleeve, a shirt, a pair of shorts, or a pair of pants and socks. In this example embodiment, article of clothing 204 is a sleeve, and in the rest of this example embodiment will be referred to as sleeve 204.

The operation of patch 202 will now be described with additional reference to FIGS. 3-4.

Figure 3:
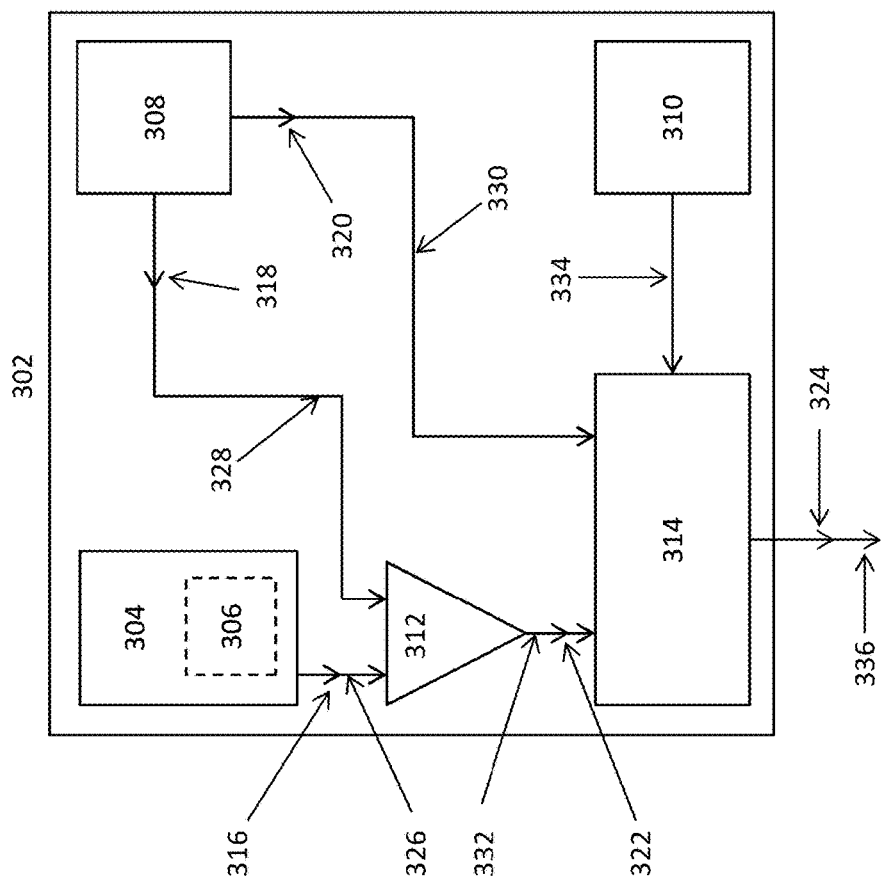
FIG. 3 illustrates a bottom side view of a patch in accordance with aspects of the present invention.

FIG. 3 illustrates a top side view of patch 202 of FIG. 2.

As illustrated in the figure, patch 202 includes a substrate 302, a material detector 304, a memory 308, a battery 310, a comparator 312, and an output component 314. Material detector 304 further includes a contact portion 308.

Substrate 302 is the base of patch 202 on which material detector 304, memory 308, battery 310, comparator 312, and output component 314 are mounted.

Material detector 304 generates a material signal 316 based on an amount of material that is in contact with contact portion 306. Material detector 304 additionally transmits material signal 316 to comparator 312, via communication line 326.

Material detector 304 further generates material signal 316 based the concentration of the material that is in contact with contact portion 306. The material that is detected by material detector 304 may be one of the group consisting of sodium (NA), potassium (K), water ($H_2O$), ammonia ($NH_3$), potential hydrogen (pH), or lactic acid (LAC). In this example embodiment, the material detected by material detector 304 is sodium.

Contact portion 306 contacts the skin of user 102 of FIG. 2. In FIG. 3, contact portion 306 is illustrated as a box created by a dashed to illustrate its placement underneath material detector 304. The location and operation of contact portion 306 will be further discussed in FIG. 4.

Memory 308 stores a priori material data that includes associations of material concentrations with respect to mass loss levels. For purposes of discussion, mass loss may be considered a difference in body mass between two times. The main contributors to mass loss include loss of water, waste materials (e.g., sweat) and fat during aerobic and anaerobic respiration. A priori data may be data previously generated by the user, or it may be data pre-loaded on memory 308 by the manufacturer, or it may be data previously generated by other users. The a priori data may include a lookup table or a database that references one or more associations between a detected material and a mass loss level. A priori data may also include functional relationships between two or more data.

Using raw a priori data or functional relationships between data may provide an output that corresponds to one or more aspects of the user's performance including, but not limited to, readiness, fitness, fatigue, and recovery time.

In some embodiments, memory 308 additionally stores a priori readiness data that includes readiness levels that are associated with mass loss levels of a material of a user.

Memory 308 further transmits the stored a priori material data as material signal 318 to comparator 312, via communication line 328. Memory 308 further transmits the a priori readiness data as signal 320 to output component 314, via communication line 330.

The a priori material data stored by memory 308 may be material data obtained from previous measurements taken from a user. Since the amount of a material detected will vary from person to person, the nominal amount of material in the system of each different user will be different as well. As such, initial measurements of an amount of material in the system of a user must be taken in order to generate a baseline value for which future measurements may be compared to.

When a user checks their physical state, the amount of material detected will be stored for future reference. Each time a user checks their physical state, additional material data will be obtained, which can be averaged with previous measurements to create a more accurate baseline.

Additionally, the a priori data stored by memory 308 may be predetermined values that are associated with loss rates of a given material. In this case, the amount of material detected in the system of a user will be the starting point for future measurements.

In this example embodiment, the a priori data that is stored by memory 308 is associated with mass loss levels of sodium detected by material detector 304, in other embodiments, the a priori data may be associated with mass loss levels of anyone of the group consisting of Na, K, $H_2O$, $NH_3$, pH, lactic acid and combinations thereof.

Battery 310 supplies power to output component 314, via line 334.

Comparator 312 compares material signal 316, from material detector 304, and material signal 318, from memory 308, in order to generate a compared signal. Comparator is additionally transmits the compared signal as mass loss level signal 322 to output component 314, via communication line 332.

In order to generate mass loss level signal 322, comparator 312 will compare the amount of material detected in the system of user 102 to the baseline amount of material in the system of user 102. Comparator 312 can then generated mass loss level signal 322 based on the amount of material in the system of user 102 compared to the baseline amount of material in the system of user 102.

Output component 314 receives signal 320 from memory 308 and mass loss level signal 322 from comparator 312. Output component 314 additionally generates readiness signal 324 based on signal 320 mass loss level signal 322. Output component 314 further wirelessly outputs readiness signal 324 to phone 106 of FIG. 2, via communication signal 336.

In order to generate readiness signal 324, output component 314 will compare mass loss level signal 322 with the a priori mass loss data, via signal 320, to find a priori data that most closely matches the data provide by user 102. When the most closely matched a priori data is found, memory 308 provides output component 314 with additional data corresponding to the a priori data. The additional data may indicate the readiness level of another that generated the a priori data. Because user 102 generated data close to the a priori data, output component 314 generates a readiness evaluation of user 102 that corresponds to mass loss, based on the a priori data.

In this example embodiment, if mass loss level signal 322 is associated with user 102 having an above average amount of sodium in their system, when output component 314 compares mass loss level signal 322 to signal 320, it will find that user 102 is in a high state of readiness.

If mass loss level signal 322 is associated with user 102 having an average amount of sodium in their system, when output component 314 compares mass loss level signal 322 to signal 320, it will find that user 102 is in a medium state of readiness. If mass loss level signal 322 is associated with user 102 having a below average amount of sodium in their system, when output component 314 compares mass loss level signal 322 to signal 320, it will find that user 102 is in a low state of readiness.

In this example, material detector 304, contact portion 306, memory 308, comparator 312, and output component 314 are illustrated as individual devices. However, in some embodiments, at least two of material detector 304, contact portion 306, memory 308, comparator 312, and output component 314 may be combined as a unitary device.

Further, in some embodiments, at least one of material detector 304, contact portion 306, memory 308, comparator 312, and output component 314 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media FIG. 4 illustrates a bottom side view of patch 202 of FIG. 2.

As illustrated in the figure, patch 202 includes substrate 302, material detector 304, contact portion 306, and an adhesive layer 402.

Contact portion 306 contacts the skin of user 102 of FIG. 2.

Adhesive layer 402 adheres substrate 302 to the skin of user 102 of FIG. 2. Adhesive layer 402 may be a pressure sensitive adhesive.

Referring back to FIG. 2, in operation, user 102 is using a fitness planner along with patch 202 to generate a training regimen based on their physical state. In this example embodiment, suppose that as a baseline, the training regimen recommends user 102 to run for three miles. The training regimen will then be adjusted according to the physical state of user 102, if user 102 is in a good physical state it will recommend user 102 to run for five miles, if user 102 is in an average physical state it will recommend user 102 to run for three miles, and if user 102 is in a poor physical state it will recommend user 102 to walk for one mile. Also suppose that in this example, user 102 has created a baseline that represents the average amount of sodium detected in their system.

In order to customize the training regimen, the physical state of user 102 must first be determined. In order to determine their physical state, user 102 begins by placing patch 202 on their arm, and then firmly pressing down on the top side of patch 202. In this example embodiment, user 102 placed patch 202 on their arm, in other embodiments, user 102 may place patch 202 on their leg, shoulder, or chest.

Figure 4:
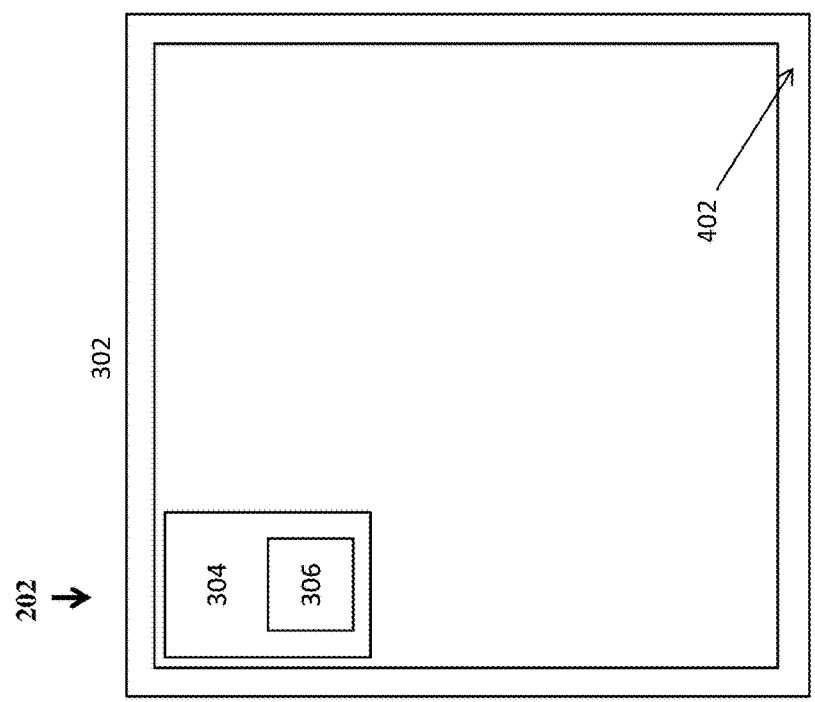
FIG. 4 illustrates a top side view of a patch in accordance with aspects of the present invention.

Briefly referring to FIG. 4, when user 102 places patch 202 in position, contact portion 306 must be contacting their skin. When user 102 applies pressure to the top side of patch 202, it activates adhesive layer 402, due to its adhesive being pressure sensitive. Once the adhesive activates, adhesive layer 402 is able to keep contact portion 306 against the skin of user 102.

It should be noted that in some embodiments, an adhesive may be used to affix patch 202 to the skin of the user, whereas in other embodiments, the pressure created by the article of clothing alone may affix patch 202 to the skin of the user. Finally, in some embodiments, a combination of an adhesive and the pressure created by the article of clothing may affix patch 202 to the skin of the user.

Referring to FIG. 3, once user 102 has placed patch 202 on their arm, applied pressure, and placed sleeve 204 on their arm to ensure that contact portion 306 is touching their skin, material detector 304 is able to detect the concentration of sodium in the system of user 102, via contact portion 306.

Once material detector 304 detects the amount of sodium in the system of user 102, it generates material signal 316 based on the detected concentration. Once generated, material detector 304 transmits material signal 316 to comparator 312, via communication line 324. Simultaneously, memory 308 accesses stored a priori data in order to locate material data that is associated with average amount of sodium in the system of user 102. Once the a priori data is located, memory 308 transmits the material data as material signal 318 to comparator 312, via communication line 328.

At this time, comparator 312 has received material signal 316, which contains the detected levels of sodium in the system of user 102, and material signal 318, which contains the a priori material data associated with the average amount of sodium in the system of user 102. Comparator 312 then compares the detected level of sodium to the a priori material data to determine if user 102 has an average, an above average or a below average amount of sodium in their system. In this example embodiment, suppose that comparator 312 finds that user 102 has an above average amount of sodium in their system. Comparator 312 then generates mass loss level signal 322 based on the amount of sodium in the system of user 102, which is then transmitted to output component 314, via communication line 332.

After output component 314 receives mass loss level signal 322, memory 308 locates stored a priori readiness data associated with mass loss levels of sodium. Once located, memory 308 generates signal 320 based on the a priori readiness data, which it then transmits to output component 314, via communication line 330.

Once output component 314 has received mass loss level signal 322 and signal 320, it can compare the two signals to determine the readiness of user 102. In this example embodiment, since user 102 has an above average amount of sodium in their system, when output component 314 compares mass loss level signal 322 and signal 320, it finds that user 102 is in a high state of readiness. At this time, output component 314 generates readiness signal 324 based on the readiness level of user 102, which it then transmits to phone 106 of FIG. 2, via communication signal 336.

Referring back to FIG. 2, once received, the training regimen of phone 106 analyzes readiness signal 324 in order to generate a recommended amount of training for the day. The training regimen then uses the baseline amount of activity along with the readiness of user 102 to generate an activity recommendation of running five miles. At this time, user 102 may begin running the recommended five miles.

Briefly referring back to FIG. 3, suppose that when comparator 312 compares the detected levels of sodium in the system of user 102 to the average amount of sodium in the system of user 102, it finds that user 102 has a below average amount of sodium in their system.

Comparator 312 will then generate mass loss level signal 322 based on the below average amount of sodium in the system of user 102, which it will then transmitted to output component 314. After output component 314 receives mass loss level signal 322, memory 308 locates stored a priori readiness data associated with mass loss levels of sodium. Once located, memory 308 generates and transmits signal 320 to output component 314.

Once output component 314 has received mass loss level signal 322 and signal 320, it can compare the two signals to determine the readiness of user 102. In this example embodiment, since user 102 has a below average amount of sodium in their system, when output component 314 compares mass loss level signal 322 and signal 320, it finds that user 102 is in a low state of readiness. Output component 314 then generates and transmits readiness signal 324 to phone 106 of FIG. 2, via communication signal 336.

Referring back to FIG. 2, once received, the training regimen of phone 106 analyzes readiness signal 324 in order to generate a recommended amount of training for the day. The training regimen then uses the baseline amount of activity along with the readiness of user 102 to generate an activity recommendation of walking one mile. At this time, user 102 may then begin walking one mile.

In the embodiments discussed above, a user's readiness is associated with an amount of detected sodium. It should be noted that this is merely a non-limiting example. In accordance with aspects of the present invention, any detectable material may be detected to evaluate a user's readiness, as long as there is a known associated with the detectable material and such readiness.

A problem with conventional systems and methods for using a fitness planner or training regimen is that there is now way to account for the physical state of a user. If a user is in a poor physical state before beginning a difficult activity, it is possible that they may hurt themselves in attempting to finish the activity.

Aspects of the present invention include a patch for application against the skin of a user in order to determine their physical state. The patch is able to determine the amount of material in the system of a user before they begin performing a physical activity. A fitness planner or training regimen can then generate a recommended amount of training based on the user's physical state.

In this manner, a user will be able to have a customized training regimen to maximize the value of their training while minimizing the risk of overexertion and physical harm caused by performing a demanded physical activity while in a poor physical state.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A patch for application against the skin of a user, said patch comprising:
   a substrate;
   a material detector disposed on said substrate and having a contact portion disposed so as to contact the skin, said material detector being operable to generate a material signal based on an amount of material contacting said contact portion;
   a memory having a priori material data and a priori readiness data stored therein;
   a comparator operable to output a compared signal based on a comparison of the material signal and the a priori material data;
   an output component operable to output a readiness signal based on the compared signal and the a priori readiness data.

2. The patch of claim 1, further comprising a pressure sensitive adhesive layer disposed on said substrate so as to adhere said substrate against said skin.

3. The patch of claim 2, wherein said material detector is operable to generate the material signal based on a concentration of the material contacting said contact portion.

4. The patch of claim 3, wherein said material detector is operable to generate the material signal based on a concentration of the material selected from one of the group consisting of K, Na, $H_2O$, $NH_3$, pH, lactic acid and combinations thereof.

5. The patch of claim 4,
   wherein said memory has a priori material data that includes associations of material concentrations with respective mass loss levels, and
   wherein said comparator is operable to output the compared signal as a mass loss level signal.

6. The patch of claim 5, wherein said output component is operable to wirelessly output the readiness signal.

7. The patch of claim 1, wherein said material detector is operable to generate the material signal based on a concentration of the material contacting said contact portion.

8. The patch of claim 7, wherein said material detector is operable to generate the material signal based on a concentration of the material selected from one of the group consisting of K, Na, $H_2O$, $NH_3$, pH, lactic acid and combinations thereof.

9. The patch of claim 8,
   wherein said memory has a priori material data that includes associations of material concentrations with respective mass loss levels, and
   wherein said comparator is operable to output the compared signal as a mass loss level signal.

10. The patch of claim 9, wherein said output component is operable to wirelessly output the readiness signal.

11. The patch of claim 10, further comprising an article of clothing supporting said substrate such that when worn by the user, said article of clothing maintains said contact portion in contact with the skin.

12. The patch of claim 11, said article of clothing comprises one of the group consisting of an arm sleeve, a leg sleeve, a shirt, a pair of shorts, a pair of pants and socks.

13. The patch of claim 1, wherein said material detector is operable to generate the material signal based on a concentration of the material selected from one of the group consisting of K, Na, $H_2O$, $NH_3$, pH, lactic acid and combinations thereof.

14. The patch of claim 1,
   wherein said memory has a priori material data that includes associations of material concentrations with respective mass loss levels, and
   wherein said comparator is operable to output the compared signal as a mass loss level signal.

15. The patch of claim 1, wherein said output component is operable to wirelessly output the readiness signal.

16. The patch of claim 1, further comprising an article of clothing supporting said substrate such that when worn by the user, said article of clothing maintains said contact portion in contact with the skin.

17. The patch of claim 16, said article of clothing comprises one of the group consisting of an arm sleeve, a leg sleeve, a shirt, a pair of shorts, a pair of pants and socks.

* * * * *